(12) United States Patent
Zones et al.

(10) Patent No.: US 7,115,198 B2
(45) Date of Patent: Oct. 3, 2006

(54) HYDROCARBON CONVERSION USING MOLECULAR SIEVE SSZ-51

(75) Inventors: Stacey I. Zones, San Francisco, CA (US); Thomas V. Harris, Benicia, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 490 days.

(21) Appl. No.: 10/691,896

(22) Filed: Oct. 22, 2003

(65) Prior Publication Data

US 2005/0087478 A1    Apr. 28, 2005

(51) Int. Cl.
*C10G 11/00*   (2006.01)
*C10G 47/16*   (2006.01)
*B01J 27/18*   (2006.01)

(52) U.S. Cl. .................. 208/113; 208/58; 208/59; 208/60; 208/111.01; 208/120.01; 208/134; 502/64; 502/67; 502/208; 585/407; 585/467; 585/475; 585/481; 585/533; 585/640; 585/671; 585/739

(58) Field of Classification Search .................. 208/58, 208/59, 60, 111.01, 113, 120.01, 134; 502/64, 502/67, 208; 585/407, 467, 475, 481, 533, 585/640, 671, 739
See application file for complete search history.

(56) References Cited

U.S. PATENT DOCUMENTS 5,935,414 A * 8/1999 Sonnemans et al. .......... 208/58
6,254,849 B1 * 7/2001 Lee et al. .................... 423/706

* cited by examiner

*Primary Examiner*—Walter D. Griffin
*Assistant Examiner*—Prem C. Singh
(74) *Attorney, Agent, or Firm*—Richard J. Sheridan (57) ABSTRACT

A novel crystalline aluminophosphate and metalloaluminophosphate of the molecular sieve type, denominated SSZ-51, is prepared by hydrothermal synthesis from reactive sources of aluminum and phosphorus, fluorine and an organic templating agent, 4-dimethylaminopyridine. SSZ-51 is useful in catalysts for, e.g., hydrocarbon conversion reactions.

58 Claims, 3 Drawing Sheets

HYDROCARBON CONVERSION USING MOLECULAR SIEVE SSZ-51

FIELD OF INVENTION

The present invention relates in general to crystalline aluminophosphate compositions, and more particularly to novel crystalline aluminophosphates and metalloaluminophosphates of the molecular sieve type, methods of its preparation and their use in catalysts for, e.g., hydrocarbon conversion reactions.

BACKGROUND OF THE INVENTION

Microporous crystalline aluminophosphate compositions having open framework structures formed of $AlO_2$ and $PO_2$ tetrahedral units joined by the sharing of the corner oxygen atoms and characterized by having pore openings of uniform dimensions have heretofore been disclosed in a number of publications, notably the specification of U.S. Pat. No. 4,310,440 issued Jul. 7, 1980, to S. T. Wilson et al. The Wilson et al. aluminophosphates constitute a generic class of non-zeolitic molecular sieve materials which are capable of undergoing complete and reversible dehydration while retaining the same essential framework topology in both the anhydrous and hydrated state. By the term "essential framework topology" or "essential framework structure" as used in the aforesaid patent, and also in the present specification and claims, is meant the spatial arrangement of the primary Al—O and P—O bond linkages. Other microporous aluminophosphates which undergo structure rearrangements, either reversibly or irreversibly, upon partial or complete dehydration are also known, for example the minerals variscite and metavariscite and certain of the synthetic metastable aluminophosphates reported by F. D'Yvoire [Bull. Soc. Chim. France, 1762 (1961)]. Another class of synthetic crystalline compositions contains framework tetrahedral metal oxides of manganese, magnesium, cobalt, and/or zinc in addition the $AlO_2$ and $PO_2$ tetrahedra. These are sometimes termed metalloaluminophosphates or MAPO'S.

SUMMARY OF THE INVENTION

The present invention provides a novel microporous crystalline aluminophosphates ("ALPO's"), aluminosilicophosphates ("APSO's"), metalloaluminophosphates ("MAPO's") and metalloaluminosilicophosphates ("MAPSO's") denominated SSZ-51 and the methods for its preparation. SSZ-51 has an essential framework structure whose chemical composition, expressed in terms of mole ratios after calcination, is:

where x has a value of 0 to 0.2 and y has a value of 0 to 0.2, z has a value of 0 to 0.10 and Me represents at least one element, other than aluminum, phosphorus or silicon, which is capable of forming an oxide in coordination with $(AlO_2)$ and $(PO_2)$ oxide structural units in the molecular sieve (such as a divalent metal). After calcination and in the hydrated state, SSZ-51 exhibits an X-ray powder diffraction pattern which contains at least the d-spacings set forth in Table II set forth hereinafter.

The framework structure of SSZ-51 consists of a building unit which is essentially a double four ring (D4R) with one disconnected (or ring-opened) edge. The fluoride ion used in synthesizing SSZ-51 is encapsulated within this building unit and forms a bridge between two of the aluminum atoms. Each building unit is then connected to four other identical building units, through two Al—O—P linkages per unit. These building units can be linked together to form the two structures, the SSZ-51 structure of this invention and a material having the structure designated AFR (e.g., SAPO-40). The building units can be joined in a "head-to-tail" fashion to form chains running parallel to the c-direction. Chains are linked together through four-rings to form undulating layers. The orientation of successive chains in these layers is anti-parellel. This layer is a building block of both SSZ-51 and AFR. The undulating layers can be linked in two ways. If the layers are linked so that there is inversion symmetry between the layers, this results in the SSZ-51 structure. If the layers are linked so that there is "mirror" symmetry between the layers the resulting structure is that of AFR (mirror symmetry here refers to the framework, i.e., excludes the need for Al/P ordering).

SSZ-51 can be prepared by hydrothermal crystallization from a reaction mixture containing in addition to water, a reactive source of aluminum, phosphorus and fluoride and an organic templating agent (sometimes referred to as a structure directing agent or "SDA") which is 4-dimethylaminopyridine. Thus, the present invention further provides a method of preparing a crystalline material comprising contacting under crystallization conditions a reaction mixture comprising a reactive source of aluminum, a reactive source of phosphorus, a reactive source of fluoride and an organic templating agent comprising 4-dimethylaminopyridine. The reaction mixture may further comprise a reactive source of a metal selected from the group consisting of magnesium, manganese, cobalt, zinc and nickel.

Thus, the present invention provides a molecular sieve whose chemical composition, expressed in terms of mole ratios of oxides after calcination, is:

where x has a value of 0 to 0.2, y has a value of 0 to 0.2, z has a value of 0 to 0.10 and Me represents at least one element, other than aluminum, phosphorus or silicon, which is capable of forming an oxide in coordination with $(AlO_2)$ and $(PO_2)$ oxide structural units in the molecular sieve, the molecular sieve having, after calcination and in the hydrated state, the X-ray diffraction lines of Table II.

The present invention further provides such a molecular sieve wherein Me is selected from the group consisting of magnesium, manganese, cobalt, zinc and nickel.

Further provided by the present invention is a molecular sieve composition, as-synthesized, whose general formula, in terms of mole ratios, is as follows:

where x has a value of 0 to 0.2, y has a value of 0 to 0.2, Q is 4-dimethylaminopyridine, z has a value of 0.02 to 0.50 and Me represents at least one element, other than aluminum, phosphorus or silicon, which is capable of forming an oxide in coordination with $(AlO_2)$ and $(PO_2)$ oxide structural units in the molecular sieve.

The present invention also provides such an as-synthesized molecular sieve wherein Me is selected from the group consisting of magnesium, manganese, cobalt, zinc and nickel.

Also provided by the present invention is such an as-synthesized molecular sieve having, in an anhydrous state, the X-ray diffraction lines of Table I.

In accordance with the present invention there is provided a process for converting hydrocarbons comprising contacting a hydrocarbonaceous feed at hydrocarbon converting conditions with a catalyst comprising the molecular sieve of this invention. The molecular sieve may be predominantly in the hydrogen form. It may also be substantially free of acidity.

Further provided by the present invention is a hydrocracking process comprising contacting a hydrocarbon feedstock under hydrocracking conditions with a catalyst comprising the molecular sieve of this invention, preferably predominantly in the hydrogen form.

This invention also includes a dewaxing process comprising contacting a hydrocarbon feedstock under dewaxing conditions with a catalyst comprising the molecular sieve of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the molecular sieve of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising the molecular sieve of this invention. The molecular sieve may be predominantly in the hydrogen form. The catalyst may contain at least one Group VIII metal.

In accordance with this invention, there is also provided a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15–3000 psi (0.103–20.7 MPa) with a catalyst comprising the molecular sieve of this invention, preferably predominantly in the hydrogen form. The catalyst may contain at least one Group VIII metal. The catalyst may be a layered catalyst comprising a first layer comprising the molecular sieve of this invention, and a second layer comprising an aluminosilicate molecular sieve which is more shape selective than the molecular sieve of said first layer. The first layer may contain at least one Group VIII metal.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. (204° C.) and at a pressure of from about 15 psig to about 3000 psig (0.103–20.7 Mpa gauge)in the presence of added hydrogen gas with a catalyst comprising the molecular sieve of this invention. The molecular sieve may be predominantly in the hydrogen form. The catalyst may contain at least one Group VIII metal.

Further included in this invention is a process for isomerization dewaxing a raffinate comprising contacting said raffinate in the presence of added hydrogen with a catalyst comprising the molecular sieve of this invention. The raffinate may be bright stock, and the molecular sieve may be predominantly in the hydrogen form. The catalyst may contain at least one Group VIII metal.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the molecular sieve of this invention made substantially free of acidity by neutralizing said molecular sieve with a basic metal. Also provided in this invention is such a process wherein the molecular sieve contains a Group VIII metal component.

Also provided by the present invention is a catalytic cracking process comprising contacting a hydrocarbon feedstock in a reaction zone under catalytic cracking conditions in the absence of added hydrogen with a catalyst comprising the molecular sieve of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the molecular sieve of this invention, preferably predominantly in the hydrogen form. The molecular sieve may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the molecular sieve of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, naphthalene, naphthalene derivatives, dimethylnaphthalene or mixtures thereof.

The present invention also provides a process for alkylating an aromatic hydrocarbon which comprises contacting under alkylation conditions an aromatic hydrocarbon with a $C_{20+}$ olefin under at least partial liquid phase conditions and in the presence of a catalyst comprising the molecular sieve of this invention, preferably predominantly in the hydrogen form. The aromatic hydrocarbon and olefin are present in a molar ratio of about 1:15 to about 25:1, respectively. The aromatic hydrocarbon is selected from the group consisting of benzene, toluene, ethylbenzene, xylene, naphthalene, naphthalene derivatives, dimethylnaphthalene or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the molecular sieve of this invention, preferably predominantly in the hydrogen form. The aromatic hydrocarbon and the polyalkyl aromatic hydrocarbon may be present in a molar ratio of from about 1:1 to about 25:1, respectively.

The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the molecular sieve of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the molecular sieve of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the molecular sieve of this invention.

The present invention further provides a process for oligomerizing olefins comprising contacting an olefin feed under oligomerization conditions with a catalyst comprising the molecular sieve of this invention.

This invention also provides a process for converting oxygenated hydrocarbons comprising contacting said oxygenated hydrocarbon with a catalyst comprising the molecular sieve of this invention under conditions to produce liquid products. The oxygenated hydrocarbon may be a lower alcohol.

Further provided in accordance with the present invention is a process for the production of higher molecular weight hydrocarbons from lower molecular weight hydrocarbons comprising the steps of:
(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and
(b) withdrawing from said reaction zone a higher molecular weight hydrocarbon-containing stream.

DETAILED DESCRIPTION OF THE INVENTION

The novel microporous aluminophosphate (or MAPO) of the present invention can be produced by hydrothermal crystallization from a reaction mixture containing reactive sources of phosphorus and aluminum and an organic templating agent (4-dimethylaminopyridine), a source of HF and, optionally, additional divalent metals or sources of silica. The preparative process typically comprises forming a reaction mixture which in terms of mole ratios is:

$Al_2O_3$:1±0.5 $P_2O_5$:0.5 HF:0.3–1.5 Q:7–100 $H_2O$ where Q is the organic templating agent 4-dimethylaminopyridine. The reaction mixture is placed in a reaction vessel inert toward the reaction mixture and heated at a temperature of at least about 100° C., preferably between 100° C. and 300° C., until crystallized, usually a period of from 2 hours to 2 weeks. The solid crystalline reaction product is then recovered by any convenient method, such as filtration or centrifugation, washed with water and dried in air at a temperature between ambient and about 100° C. In a preferred crystallization method, the source of phosphorus is phosphoric acid, and the source of aluminum is a hydrated aluminum oxide of the trade name Catapal, the temperature is 150° C. to 200° C., the crystallization time is from 2 to 7 days, and the ratio of compounds in the reaction mixture is $Al_2O_3$:0.8–1.2 $P_2O_5$:0.5 HF:0.5–0.75 Q:25–75 $H_2O$

The templating agent is 4-dimethylaminopyridine having the structure 4-dimethylamino pyridine and is present in the reaction mixture in an amount of from about 0.5 to 0.75 moles per mole of alumina. Additionally present may be sources of divalent metals such as magnesium, manganese, cobalt, zinc, nickel and so forth. In these instances it is anticipated that these metals will replace Al in the lattice so the amount of Al provided in the synthesis is reduced accordingly. Silica may also be introduced into the reaction. Typically, silicon will replace P in the lattice, so the amount of P provided in the synthesis is reduced accordingly.

The template-containing as-synthesized form of SSZ-51 has an essential framework structure whose chemical composition expressed in terms of mole ratios is:

$Al_2O_3$:1.0±0.2 $P_2O_5$:0.5±0.2 Q:x $SiO_2$:y MeO:z F where x, y, Me and z are as defined above. As-synthesized SSZ-51, in an anhydrous state, has a characteristic X-ray powder diffraction pattern which contains at least the d-spacings set forth in Table I below.

TABLE I

Characteristic peaks of as-synthesized SSZ-51

| 2 Theta[a] | d-spacing (Angstroms) | Relative Intensity (%)[b] |
|---|---|---|
| 7.6 | 11.7 | S |
| 8.2 | 10.8 | VS |
| 13.9 | 6.4 | VS |
| 14.1 | 6.3 | S |
| 18.9 | 4.7 | W |
| 19.1 | 4.6 | W-M |
| 19.7 | 4.5 | S |
| 20.0 | 4.4 | W-M |
| 25.8 | 3.5 | S |
| 26.1 | 3.42 | M |

[a]±0.1
[b]The X-ray patterns provided are based on a relative intensity scale in which the strongest line is assigned a value of 100: W (weak) is less than 20; M (medium) is between 20 and 40; S (strong) is between 40 and 60; VS (very strong) is greater than 60.

The complete X-ray powder diffraction pattern, including actual relative intensities, for anhydrous, as-synthesized SSZ-51 is set forth in Table IA below.

TABLE IA

Peaks of as-synthesized SSZ-51

| 2 Theta | d-spacing (Angstroms) | Relative Intensity (%) |
|---|---|---|
| 7.56 | 11.69 | 53.8 |
| 8.18 | 10.81 | 100.0 |
| 12.52 | 7.07 | 15.3 |
| 12.78 | 6.93 | 4.6 |
| 13.88 | 6.38 | 85.4 |
| 14.09 | 6.28 | 48.0 |
| 15.22 | 5.82 | 11.2 |
| 16.46 | 5.39 | 6.6 |
| 18.94 | 4.69 | 17.2 |
| 19.10 | 4.65 | 21.6 |
| 19.70 | 4.51 | 52.2 |
| 20.02 | 4.44 | 19.3 |
| 20.96 | 4.24 | 6.4 |
| 21.62 | 4.11 | 3.2 |
| 22.28 | 3.99 | 4.0 |
| 22.62 | 3.93 | 4.9 |
| 22.94 | 3.88 | 15.2 |
| 23.30 | 3.82 | 6.4 |
| 24.88 | 3.58 | 3.4 |
| 25.32 | 3.52 | 8.1 |
| 25.78 | 3.46 | 51.3 |
| 26.08 | 3.42 | 22.4 |
| 26.74 | 3.33 | 10.7 |
| 27.10 | 3.29 | 7.5 |
| 27.86 | 3.20 | 9.9 |
| 28.42 | 3.14 | 3.7 |
| 28.80 | 3.10 | 3.3 |
| 29.14 | 3.06 | 4.2 |
| 29.44 | 3.03 | 6.9 |
| 29.72 | 3.01 | 6.4 |
| 30.56 | 2.93 | 8.2 |
| 30.84 | 2.90 | 6.2 |
| 31.64 | 2.83 | 2.7 |
| 32.4 | 2.76 | 5.3 |

When the as-synthesized SSZ-51 compositions are calcined, i.e., heated at a temperature sufficiently high, typically between about 300° C. and about 700° C., or otherwise treated, such as by chemical oxidation, to remove essentially all of the organic templating agent present in the intracrystalline pore system and then rehydrated, the composition has an X-ray powder diffraction pattern which contains at least the d-spacings set forth in Table II below:

TABLE II

Characteristic peaks of calcined and hydrated SSZ-51

| 2 Theta | d-spacing (Angstroms) | Relative Intensity (%) |
|---|---|---|
| 7.70 | 11.51 | VS |
| 8.08 | 10.9 | VS |
| 13.18 | 6.7 | W |
| 13.80 | 6.4 | W |
| 14.02 | 6.3 | W |
| 16.64 | 5.32 | W |
| 20.20 | 4.39 | M |
| 22.44 | 3.96 | W |
| 23.28 | 3.82 | W |
| 26.62 | 3.35 | M |
| 30.02 | 2.97 | W-M |

A complete X-ray powder diffraction pattern (synchrotron, 0.704 Angstrom), including actual relative intensities, for calcined, rehydrated SSZ-51 is set forth in Table IIA below. Intensities were determined by LeBail intensity extraction of the pattern.

TABLE IIA

Peaks of calcined, rehydrated SSZ-51

| 2 Theta | d-spacing (Angstroms) | Relative Intensity (%) |
|---|---|---|
| 3.45 | 11.7 | 100 |
| 3.63 | 11.1 | 63 |
| 5.81 | 6.95 | 12.2 |
| 5.87 | 6.87 | 2.7 |
| 6.19 | 6.52 | 9.9 |
| 6.52 | 6.19 | 13.2 |
| 6.98 | 5.78 | 1.3 |
| 7.27 | 5.54 | 1.9 |
| 7.92 | 5.10 | 2.3 |
| 8.61 | 4.69 | 10.7 |
| 8.68 | 4.65 | 5.7 |
| 9.00 | 4.48 | 23.2 |
| 9.36 | 4.32 | 14.8 |
| 9.55 | 4.23 | 4.6 |
| 10.02 | 4.03 | 3.1 |
| 10.36 | 3.90 | 10.2 |
| 10.45 | 3.87 | 2.1 |
| 11.57 | 3.49 | 10.9 |
| 11.76 | 3.43 | 7.4 |
| 11.87 | 3.40 | 15.6 |
| 12.29 | 3.29 | 1.9 |
| 12.38 | 3.26 | 5.0 |
| 12.67 | 3.19 | 5.9 |
| 12.78 | 3.16 | 2.9 |

The room temperature powder X-ray diffraction pattern of SSZ-51 changes dramatically after calcination to remove the occluded organic SDA and fluoride ions. There seems to be a distinct loss of crystallinity, with diffraction peaks for the calcined sample being much broader and less well defined than for the uncalcined sample. It would appear that the calcination procedure has probably resulted in some breakdown of the framework structure. However, calcined SSZ-51 possesses appreciable microporosity (close to FAU-type molecular sieves), and the density functional theory (DFT) measurements indicate the likely presence of 12- and 8-rings. This is consistent with the removal of fluoride and SDA while retaining the framework structure intact. These two results are therefore seemingly at odds. In order to follow the calcination process, variable temperature powder X-ray diffraction data on the as-made sample was collected in order to monitor structural changes as SSZ-51 is heated in air.

Figure 3:
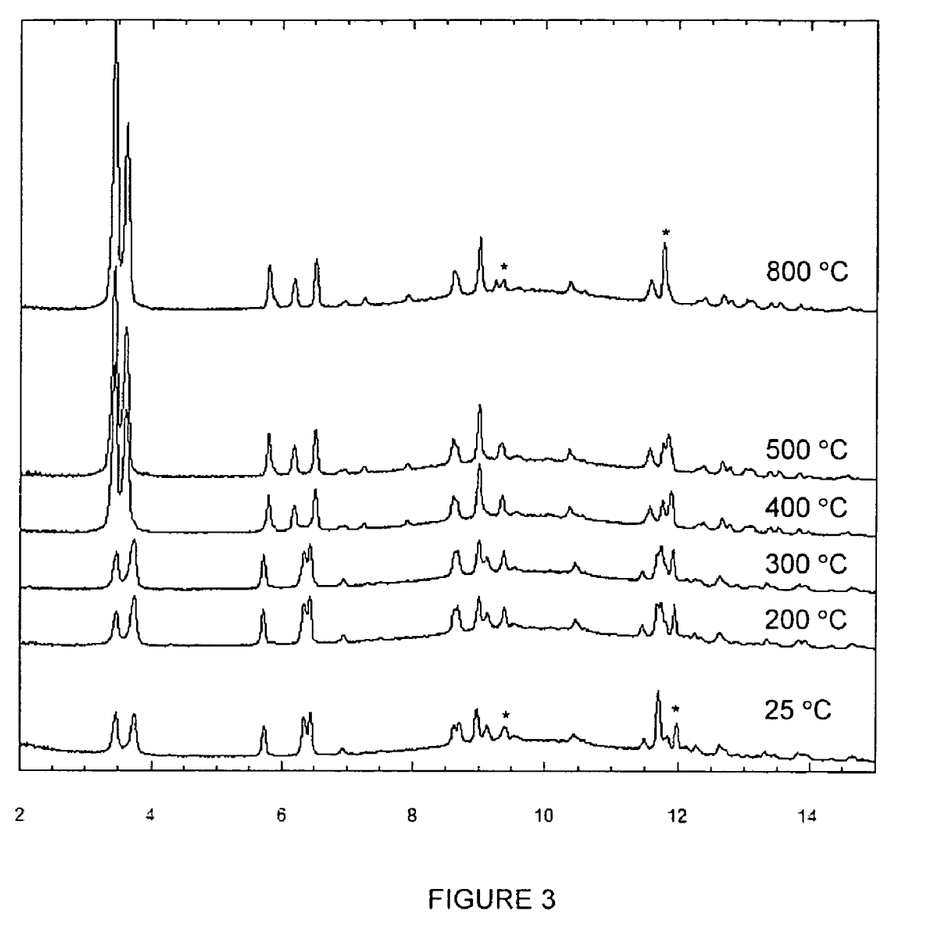
FIG. 3 is a series of X-ray patterns (synchrotron, 0.704 Angstrom) of as-made SSZ-51 as it is being calcined. The * indicates berlinite peaks.

FIG. 3 shows the effect of temperature on the powder diffraction pattern of the as-made sample of SSZ-51. The data were collected at a synchrotron with a wavelength of about 0.704 Angstrom with samples in rotating capillaries. Note the presence of peaks due to berlinite (the AlPO analogue of quartz). As the material is heated to 300° C., there are only slight changes in the XRD pattern. However, at 400° C. there are dramatic changes in both the peak positions and intensities as the SDA and fluoride are removed from the structure. The shifts are readily apparent in the positions of the (110), (200), and (310) reflections. This XRD pattern can be indexed by a C-centered monoclinic cell with lattice parameters of a=22.4, b=13.7, c=14.0, $\beta$=98.5° (as verified by a LeBail profile fit). While the other lattice parameters show little change, the a lattice parameter increases by 3.3%. This change seems mostly due to the relaxation of the framework as the fluoride bonds with the framework are broken.

After 400° C., there is little variation in the pattern due to structural changes in SSZ-51.

Figure 1:
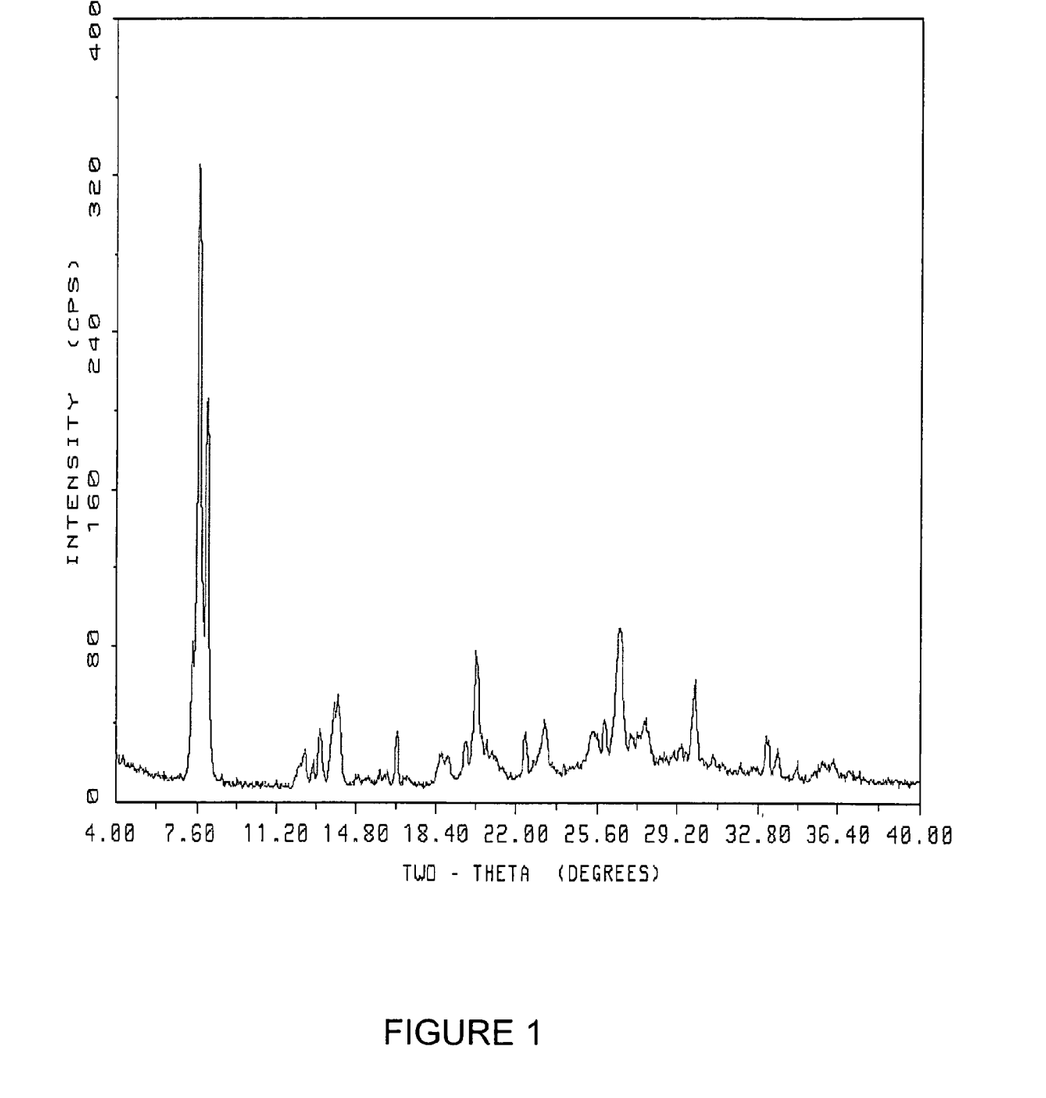
FIG. 1 is an X-ray pattern (CuKα) of calcined and hydrated SSZ-51.
Figure 2:
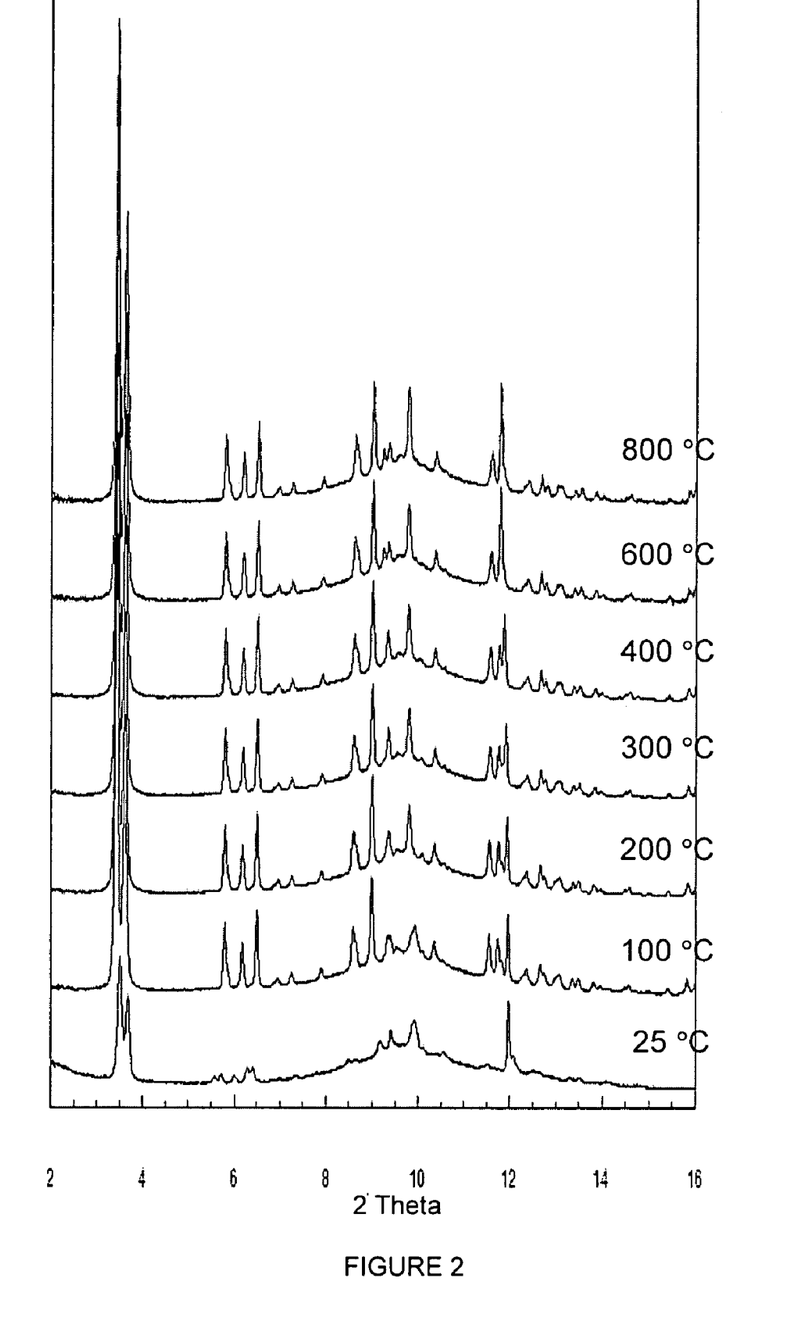
FIG. 2 is a series of X-ray patterns (synchrotron, 0.704 Angstrom) illustrating the change in the pattern as calcined and rehydrated SSZ-51 is dehydrated.

The good thermal stability of SSZ-51 is quite surprising in that the material survives calcination to 800° C. while retaining a quite crystalline structure. This is at odds with the room temperature XRD pattern, which shows a distinct loss of crystallinity. This change in XRD pattern must then be due to the rehydration of the framework rather than any inherent thermal instability of the framework. On leaving the calcined SSZ-51 in moist air for a day the broad diffraction pattern of FIG. 2 is again recorded. However, on heating the sample to 100° C., the diffraction pattern reverts to that which we expect for a highly crystalline sample of SSZ-51, with most of the expected reflections from the unit cell distinctly visible. It would appear that the rehydration process affects the crystallinity of the SSZ-51 framework markedly. A similar effect is seen in the thermal treatment of SAPO-40, which has the related AFR framework structure described above. Once again, the structure of the framework is grossly changed by the addition of water at room temperature, removing the long range order in the structure and producing an X-ray diffraction containing broad Bragg peaks. In both SSZ-51 and SAPO-40, this behavior is probably closely linked to the addition of water to the framework aluminum atoms, producing 5- and perhaps 6-coordinated aluminum atoms and so distorting the structure away from that found for the dehydrated framework.

X-ray diffraction data was collected at a synchrotron source with a wavelength of about 0.704 Angstrom. Interplanar spacings (d) in Angstrom units are obtained from the position of the diffraction peaks expressed as 2θ (theta) as observed on the strip chart where theta is the Bragg angle. Intensities were determined from the heights of diffraction peaks after subtracting background, "$I_o$" being the intensity of the strongest line or peak, and "I" being the intensity of each of the other peaks.

As will be understood by those skilled in the art the determination of the parameter 2 theta, irrespective of the technique employed, is subject to both human and mechanical error, which in combination, can impose an uncertainty of about 0.1° on each reported value of 2 theta. This uncertainty is, of course, also manifested in the reported value of the d-spacings, which are calculated from the 2 theta values. This imprecision is general throughout the art and is not sufficient to preclude the differentiation of the present crystalline materials from the compositions of the prior art. In some of the X-ray patterns reported, the relative intensities of the d-spacings are indicated by the notations VS, S, M, and W which represent Very Strong, Strong, Medium, and Weak, respectively.

SSZ-51 exhibits surface characteristics which make it useful as a catalyst or catalyst support in various hydrocarbon conversion and oxidative combustion processes. SSZ-51 can be associated with catalytically active metals, e.g., by framework substitution, by impregnation, doping and the like, by methods traditionally used in the art for the fabrication of catalyst compositions.

Further, SSZ-51 has a pore size of less than about 8 Angstroms which makes SSZ-51 suitable for use as a molecular sieve for the separation of molecular species. In addition, SSZ-51 is useful in catalysts for hydrocarbon conversion reactions such as hydrocracking, dewaxing and the like.

Hydrocarbon Conversion Processes

SSZ-51 molecular sieves are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-51 are expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives, and forming higher molecular weight hydrocarbons from lower molecular weight hydrocarbons (e.g., methane upgrading). The SSZ-51 catalysts may have high selectivity, and under hydrocarbon conversion conditions can provide a high percentage of desired products relative to total products.

For high catalytic activity, the SSZ-51 molecular sieve should be predominantly in its hydrogen ion form. Generally, the molecular sieve is converted to its hydrogen form by ammonium exchange followed by calcination. If the molecular sieve is synthesized with a high enough ratio of SDA cation to sodium ion, calcination alone may be sufficient. It is preferred that, after calcination, at least 80% of the cation sites are occupied by hydrogen ions and/or rare earth ions. As used herein, "predominantly in the hydrogen form" means that, after calcination, at least 80% of the cation sites are occupied by hydrogen ions and/or rare earth ions.

SSZ-51 molecular sieves can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-51 in the hydrocarbon conversion reactions of this invention. Preferred conditions are indicated in parentheses.

| Process | Temp., ° C. | Pressure | LHSV |
|---|---|---|---|
| Hydrocracking | 175–485 | 0.5–350 bar | 0.1–30 |
| Dewaxing | 200–475 (250–450) | 15–3000 psig, 0.103–20.7 Mpa gauge (200–3000, 1.38–20.7 Mpa gauge) | 0.1–20 (0.2–10) |

-continued

| Process | Temp., °C. | Pressure | LHSV |
|---|---|---|---|
| Aromatics formation | 400–600 (480–550) | atm.-10 bar | 0.1–15 |
| Cat. Cracking | 127–885 | subatm.-[1] (atm.-5 atm.) | 0.5–50 |
| Oligomerization | 232–649[2] 10–232[4] (27–204)[4] | 0.1–50 atm.[2,3] — — | 0.2–50[2] 0.05–20[5] (0.1–10)[5] |
| Paraffins to aromatics | 100–700 | 0–1000 psig | 0.5–40[5] |
| Condensation of alcohols | 260–538 | 0.5–1000 psig, 0.00345–6.89 Mpa gauge | 0.5–50[5] |
| Isomerization | 93–538 (204–315) | 50–1000 psig, 0.345–6.89 Mpa gauge | 1–10 (1–4) |
| Xylene isomerization | 260–593[2] (315–566)[2] 38–371[4] | 0.5–50 atm.[2] (1–5 atm)[2] 1–200 atm.[4] | 0.1–100[5] (0.5–50)[5] 0.5–50 |

[1]Several hundred atmospheres
[2]Gas phase reaction
[3]Hydrocarbon partial pressure
[4]Liquid phase reaction
[5]WHSV
Other reaction conditions and parameters are provided below.

Hydrocracking

Using a catalyst which comprises SSZ-51, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. Nos. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-51, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-51 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel) (0.089 to 5.34 SCM/liter (standard cubic meters/liter)), preferably about 1000 to about 20,000 SCF/bbl (0.178 to 3.56 SCM/liter). Generally, hydrogen will be separated from the product and recycled to the reaction zone. Typical feedstocks include light gas oil, heavy gas oils and reduced crudes boiling above about 350° F. (177° C.).

A typical dewaxing process is the catalytic dewaxing of a hydrocarbon oil feedstock boiling above about 350° F. (177° C.) and containing straight chain and slightly branched chain hydrocarbons by contacting the hydrocarbon oil feedstock in the presence of added hydrogen gas at a hydrogen pressure of about 15–3000 psi (0.103–20.7 Mpa) with a catalyst comprising SSZ-51 and at least one Group VIII metal.

The SSZ-51 hydrodewaxing catalyst may optionally contain a hydrogenation component of the type commonly employed in dewaxing catalysts. See the aforementioned U.S. Pat. Nos. 4,910,006 and 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isomerization dewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-51 may also be utilized as a dewaxing catalyst in the form of a layered catalyst. That is, the catalyst comprises a first layer comprising molecular sieve SSZ-51 and at least one Group VIII metal, and a second layer comprising an aluminosilicate molecular sieve which is more shape selective than molecular sieve SSZ-51. The use of layered catalysts is disclosed in U.S. Pat. No. 5,149,421, issued Sep. 22, 1992 to Miller, which is incorporated by reference herein in its entirety. The layering may also include a bed of SSZ-51 layered with a non-zeolitic component designed for either hydrocracking or hydrofinishing.

SSZ-51 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig (2.76 to 20.7 Mpa gauge) at space velocities (LHSV) between about 0.1 and 20 and a hydrogen recycle rate of about 400 to 1500 SCF/bbl (0.071 to 0.27 SCM/liter). The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-51. For example, a $C_{20+}$ lube oil may be made by isomerizing a $C_{20+}$ olefin feed over a catalyst comprising SSZ-51 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. (204° C.) and at a pressure of from about 15 psig to about 3000 psig (0.103–20.7 Mpa gauge) in the presence of added hydrogen gas with a catalyst comprising SSZ-51 in the hydrogen form and at least one Group VIII metal.

Aromatics Formation

SSZ-51 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising SSZ-51. It is also possible to convert heavier feeds into BTX or naphthalene derivatives of value using a catalyst comprising SSZ-51.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the molecular sieve with a basic metal, e.g., alkali metal, compound. Methods for rendering the catalyst free of acidity are known in the art. See the aforementioned U.S. Pat. Nos. 4,910,006 and 5,316,753 for a description of such methods.

The preferred alkali metals are sodium, potassium, rubidium and cesium. The molecular sieve itself can be substantially free of acidity only at very high silica:alumina mole ratios.

Catalytic Cracking

Hydrocarbon cracking stocks can be catalytically cracked in the absence of hydrogen using SSZ-51, preferably predominantly in the hydrogen form.

When SSZ-51 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. Nos. 4,910,006 and 5,316,753. When a traditional cracking catalyst (TC) component is employed, the relative weight ratio of the TC to the SSZ-51 is generally between about 1:10 and about 500:1, desirably between about 1:10 and about 200:1, preferably between about 1:2 and about 50:1, and most preferably is between about 1:1 and about 20:1. The novel molecular sieve and/or the traditional cracking component may be further ion exchanged with rare earth ions to modify selectivity.

The cracking catalysts are typically employed with an inorganic oxide matrix component. See the aforementioned U.S. Pat. Nos. 4,910,006 and 5,316,753 for examples of such matrix components.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-51 in the hydrogen form, with a hydrocarbon feed under isomerization conditions. The feed is preferably a light straight run fraction, boiling within the range of 30° F. to 250° F. (−1° C. to 121° C.) and preferably from 60° F. to 200° F. (16° C. to 93° C.). Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. See the aforementioned U.S. Pat. Nos. 4,910,006 and 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. Nos. 4,910,006 and 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. Nos. 4,910,006 and 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-51 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-51.

SSZ-51 can also be used for removing benzene from gasoline by alkylating the benzene as described above and removing the alkylated product from the gasoline.

For high catalytic activity, the SSZ-51 molecular sieve should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene or naphthalene derivatives such as dimethylnaphthalene may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F. (38° C. to 315° C.), preferably 250° F. to 450° F. (121° C. to 232° C.). The reaction pressure should be sufficient to maintain at least a partial liquid phase in order to retard catalyst fouling. This is typically 50 psig to 1000 psig (0.345 to 6.89 Mpa gauge) depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F. (38° C. to 315° C.), but it is preferably about 250° F. to 450° F. (121° C. to 232° C.). The reaction pressure should be sufficient to maintain at least a partial liquid phase, typically in the range of about 50 psig to 1000 psig (0.345 to 6.89 Mpa gauge), preferably 300 psig to 600 psig (2.07 to 4.14 Mpa gauge). The weight hourly space velocity will range from about 0.1 to 10. U.S. Pat. No. 5,082,990 issued on Jan. 21, 1992 to Hsieh, et al. describes such processes and is incorporated herein by reference.

SSZ-51 can also be used to alkylate aromatics compounds using $C_{20+}$ olefins. These alkylated aromatics can then be converted to sulfonic acids or sulfonates and used as additives in lubricating oils. Such an alkylation process is disclosed in U.S. Pat. No. 5,922,922, issued Jul. 13, 1999 to Harris et al., which is incorporated by reference in its entirety.

The aromatic hydrocarbon that is alkylated in this process is preferably benzene or toluene, but a higher molecular weight hydrocarbon may also be used. The feed aromatic hydrocarbon may, therefore be benzene, toluene, xylene, naphthalene, etc. Preferably it is benzene or toluene, because the resulting alkylates are more easily processed into the corresponding sulfonic acids or LOB or HOB sulfonates.

The olefinic hydrocarbons that are consumed in the process are normal alpha-olefins (NAO) that may have from about six to thirty carbon atoms per molecule. Preferably, they have about fourteen to thirty carbon atoms per molecule. Most preferably, they are predominantly alpha olefins having from twenty to twenty-eight carbon atoms per molecule.

The NAO is isomerized with an acidic catalyst prior to alkylation. Preferably, the catalyst is a molecular sieve with a one-dimensional pore system such as SM-3, MAPO-11, SAPO-11, SSZ-32, ZSM-23, MAPO-39, SAPO-39, ZSM-22 and SSZ-20. Other possible solid acidic catalysts include ZSM-35, SUZ-4, NU-23, NU-87 and natural or synthetic ferrierites.

The isomerization process conditions are well known in the art. See, for example, aforementioned U.S. Pat. No. 5,922,922.

SSZ-5 1, in acidic form, is used as the alkylation catalyst. Preferably, it is used predominantly in the hydrogen form.

The alkylation process conditions are likewise well known in the art. The alkylation reaction is typically carried out with an aromatic to olefin mole ratio from 1:15 to 25:1. Process temperatures can range from 100° C. to 250° C. As the olefins have a high boiling point, the process is preferably carried out in the liquid phase.

Conversion of Paraffins to Aromatics

SSZ-51 can be used to convert light gas $C_2$–$C_6$ paraffins to higher molecular weight hydrocarbons including aromatic compounds. Preferably, the molecular sieve will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Isomerization of Olefins

SSZ-51 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40–60 weight percent normal butenes. A methyl-tert-butyl ether unit effluent typically contains 40–100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the SSZ-51. The process may be carried out generally at a temperature from about 625° F. to about 950° F. (329–510° C), for butenes, preferably from about 700° F. to about 900° F. (371–482° C.), and about 350° F. to about 650° F. (177–343° C.) for pentenes and hexenes. The pressure ranges from subatmospheric to about 200 psig (1.38 Mpa gauge), preferably from about 15 psig to about 200 psig (0.103 to 1.38 Mpa gauge), and more preferably from about 1 psig to about 150 psig (0.00689 to 1.03 Mpa gauge).

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Xylene Isomerization

SSZ-51 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt. of a diluent such as toluene, trimethylbenzene, naphthenes or paraffins.

Oligomerization

It is expected that SSZ-51 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-51.

The molecular sieve can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the molecular sieve have a fairly low aromatization activity, i.e., in which the amount of aromatics produced is not more than about 20% by weight. This is accomplished by using a molecular sieve with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such molecular sieves may be obtained by steaming, by use in a conversion process or by any other method which may occur to one skilled in this art.

Condensation of Alcohols

SSZ-51 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Methane Upgrading

Higher molecular weight hydrocarbons can be formed from lower molecular weight hydrocarbons by contacting the lower molecular weight hydrocarbon with a catalyst comprising SSZ-51 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide, actinide, molybdenum and/or niobium metals or metal compounds.

These reactions, the metals or metal compounds employed and the conditions under which they can be run are disclosed in U.S. Pat. No. 4,734,537, issued Mar. 29, 1988 to Devries et al.; U.S. Pat. No. 4,939,311, issued Jul. 3, 1990 to Washecheck et al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

The following examples are provided to illustrate the invention and are not to be construed as limiting thereof:

EXAMPLE 1

Synthesis of SSZ-51

SSZ-51 is prepared by combining 1.33 grams of a hydrated aluminum oxide, a pseudo-boehmite phase comprising 75.1 weight percent $Al_2O_3$ and 24.9 weight percent $H_2O$, with a solution of 2.2 grams of 85 wt % orthophosphoric acid ($H_3PO_4$) and 9 grams of $H_2O$. The resulting mixture is stirred until a homogeneous mixture is observed. This mixture is then mixed with 0.22 grams of 50% HF and the resulting mixture stirred until homogeneous. To the above mixture 0.90 grams of 4-dimethylaminopyridine (DMAP) is added and then 0.06 grams of Cabosil M-5 amorphous fumed silica and the resultant mixture is once again mixed until homogeneous. The composition of reaction mixture in molar ratios is:

0.75 DMAP:$Al_2O_3$:$P_2O_5$:0.5 HF:0.1 $SiO_2$:50 $H_2O$

The reaction mixture is sealed in a stainless steel pressure vessel lined with polytetrafluoroethylene and heated in an oven at 180° C. at autogenous pressure for 50 hours. The solid reaction product is recovered by filtration, washed with water and dried in air at ambient temperature.

A portion of the solid reaction product is analyzed and the following chemical analysis obtained:

1.26 wt % Si, 16.21 wt % Al, 17.75 wt % P and 1.10 wt % F

The organic content was not obtained in this analysis.

The solid reaction product is analyzed by X-ray powder diffraction and found to be SSZ-51.

EXAMPLES 2–9

Synthesis of SSZ-51

In a manner similar to Example 1, SSZ-51 is prepared using the starting materials and conditions shown in Table A below. Elemental analysis for some of the products is shown in Table B below where the numbers are weight percent.

TABLE A

| Ex. No. | $H_2O$ | HF | $H_3PO_4$ | Cabosil M-5 or metal | DMAP | $Al_2O_3$[1] | Temp., ° C. | Time (Days) |
|---|---|---|---|---|---|---|---|---|
| 2 | 9 g | 0.33 g | 2.20 g | 0.06 g[2] | 0.90 g | 1.33 g | 180 | 2.5 |
| 3 | 9 g | 0.33 g | 2.20 g | 0.12 g[2] | 0.90 g | 1.33 g | 180 | 6 |
| 4 | 9 g | 0.22 g | 2.0 g | Co[3] | 1.20 g | 1.33 g | 180 | 2.5 |
| 5 | 9 g | 0.33 g | 2.2 g | Co[3] | 0.90 g | 1.20 g | 180 | 2.5 |
| 6 | 9 g | 0.22 g | 2.2 g | Co[3] | 0.90 g | 1.26 g | 180 | 2.5 |
| 7 | 9 g | 0.22 g | 2.2 g | Ni[3] | 0.90 g | 1.26 g | 160 | 4 |
| 8 | 9 g | 0.22 g | 2.2 g | Zn[3] | 0.90 g | 1.26 g | 160 | 4 |
| 9 | 9 g | 0.22 g | 2.2 g | Mg[3] | 0.90 g | 1.26 g | 160 | 4 |

[1]Hydrated aluminum oxide, 75.1 wt. % $Al_2O_3$ and 24.9 wt. % $H_2O$
[2]Cabosil M-5
[3]1 mmole added as nitrate salt

TABLE B

| Ex. No. | Al | P | Si | Co | F | Ni | Zn | Mg |
|---|---|---|---|---|---|---|---|---|
| 1 | 16.1 | 17.75 | 1.26 | | 1.10 | | | |
| 5 | 15.95 | 19.72 | | 1.91 | 2.33 | | | |
| 7 | 14.94 | 18.79 | | | 2.12 | 3.08 | | |
| 8 | 14.57 | 20.06 | | | 1.74 | | 1.73 | |
| 9 | 16.92 | 20.20 | | | 1.46 | | | 0.34 |

COMPARATIVE EXAMPLE A

A reaction is conducted using the reactants and procedure of Example 1, except that no HF was used. The crystalline product is determined by X-ray analysis to be SAPO-5. This example demonstrates that, when HF is left out of the reaction mixture, SAPO-5 is the product rather than SSZ-51.

EXAMPLE 10

Unit Cell from Synchrotron Data

Data is collected on the product of Example 1 with the following experimental parameters: A wavelength of 0.6875Angstroms (Silicon 111 monochromator) is used in conjunction with Bruker-Nonius goniometer equipped with a 1K CCD area detector and temperature controlled to 150° K. The determination is made that the crystalline solid has, for a monoclinic, C2/c space group the following lattice parameters:

a=21.759(3) Angstroms b=13.8214(18) Angstroms, Beta=98.849(4) deg.

c=14.2237 (18) Angstroms

EXAMPLE 11

Calcination of SSZ-51

The material from Example 1 is calcined in the following manner. A thin bed of material is heated in a muffle furnace from room temperature to 120° C. at a rate of 1° C. per minute and held at 120° C. for three hours. The temperature is then ramped up to 540° C. at the same rate and held at this temperature for 5 hours, after which it is increased to 594° C. and held there for another 5 hours. A 50/50 mixture of air and nitrogen is passed over the SSZ-51 at a rate of 20 standard cubic feet per minute during heating.

EXAMPLE 12

Argon Adsorption Analysis

SSZ-51 has a micropore volume (t-plot) of 0.25 cc/gm based on argon adsorption isotherm at 87.3 K recorded on ASAP 2010 equipment from Micromeritics. The low-pressure dose was 2.00 cm$^3$/g (STP) with 15-s equilibration interval. The argon adsorption isotherm is analyzed using the density function theory (DFT) formalism and parameters developed for activated carbon slits by Olivier (*Porous Mater.* 1995, 2, 9) using the Saito Foley adaptation of the Horvath-Kawazoe formalism (*Microporous Materials,* 1995, 3, 531) and the conventional t-plot method (*J. Catalysis,* 1965, 4, 319). The DFT analysis also shows that SSZ-51 has at least one large pore.

EXAMPLE 13

Calcination of SSZ-51

The product of Example 6 is calcined in the manner described in Example 11.

EXAMPLE 14

Constraint Index Determination

The hydrogen form of the SSZ-51 of Example 13 is pelletized at 2–3 KPSI, crushed and meshed to 20–40, and then >0.50 gram is calcined at about 540° C. in air for four hours and cooled in a desiccator. 0.50 Gram is packed into a ⅜ inch stainless steel tube with alundum on both sides of the molecular sieve bed. A Lindburg furnace is used to heat the reactor tube. Helium is introduced into the reactor tube at 10 cc/min. and at atmospheric pressure. The reactor is heated to about 800° F. (427° C.), and a 50/50 (w/w) feed of n-hexane and 3-methylpentane is introduced into the reactor at a rate of 8 µl/min. Feed delivery is made via a Brownlee pump. Direct sampling into a gas chromatograph begins after 10 minutes of feed introduction. The Constraint Index value is calculated from the gas chromatographic data using methods known in the art. SSZ-51 has a Constraint Index of 0.4–0.5 at a feed conversion of 40% at 800° F. (427° C.) after 10 minutes. The Constraint-Index dropped with time on stream. The Constraint Index values over this period continue to show large pore molecular sieve behavior.

EXAMPLE 15

Hydrocracking of n-Hexadecane

A sample of SSZ-51 as prepared in Example 13 is impregnated with Pd(NH$_3$)$_4$(NO$_3$)$_2$ salt using water and giving a 0.5 wt. % Pd value with respect to the dry weight of the molecular sieve sample. This slurry is stirred for 48 hours at room temperature. After cooling, the slurry is filtered through a glass frit, washed with de-ionized water, and dried at 100° C. The catalyst is then calcined slowly up to 482° C. (900° F.) in air and held there for three hours.

The calcined catalyst is pelletized in a Carver Press and crushed to yield particles with a 20/40 mesh size range. Sized catalyst (0.5 g) is packed into a ¼ inch OD tubing reactor in a micro unit for n-hexadecane hydroconversion.

A balance of isomerization and cracking is observed as the catalyst is taken through a regime of 30% conversion at 600° F. (315° C.) to 90% at 667° F. (353° C). The cracking increases with temperature. The test is run at a WHSV of 1.55 at 1200 psig and without titration. Very little $C_1$ and $C_2$ are observed and the iso/n ratios for $C_4$ and larger are indicative of large pore selectivity.

What is claimed is:

1. A process for converting hydrocarbons comprising contacting a hydrocarbonaceous feed at hydrocarbon converting conditions with a catalyst comprising a molecular sieve whose chemical composition, expressed in terms of mole ratios of oxides after calcination, is:

$Al_2O_3$:1.0±0.2 $P_2O_5$: $x$ $SiO_2$: $y$ MeO ; $z$ F where x has a value of 0 to 0.2, y has a value of 0 to 0.2, z has a value of 0 to 0.10 and Me represents at least one element, other than aluminum, phosphorus or silicon, which is capable of forming an oxide in coordination with (AlO$_2$) and (PO$_2$) oxide structural units in the molecular sieve, the molecular sieve having, after calcination and in a hydrated state, the X-ray diffraction lines of Table II.

2. The process of claim 1 wherein the molecular sieve is predominantly in the hydrogen form.

3. The process of claim 1 wherein the molecular sieve is substantially free of acidity.

4. The process of claim 1 wherein the process is a hydrocracking process comprising contacting the catalyst with a hydrocarbon feedstock under hydrocracking conditions.

5. The process of claim 4 wherein the molecular sieve is predominantly in the hydrogen form.

6. The process of claim 1 wherein the process is a dewaxing process comprising contacting the catalyst with a hydrocarbon feedstock under dewaxing conditions.

7. The process of claim 6 wherein the molecular sieve is predominantly in the hydrogen form.

8. The process of claim 1 wherein the process is a process for improving the viscosity index of a dewaxed product of waxy hydrocarbon feeds comprising contacting the catalyst with a waxy hydrocarbon feed under isomerization dewaxing conditions.

9. The process of claim 8 wherein the molecular sieve is predominantly in the hydrogen form.

10. The process of claim 1 wherein the process is a process for producing a $C_{20+}$ lube oil from a $C_{20+}$ olefin feed comprising isomerizing said olefin feed under isomerization conditions over the catalyst.

11. The process of claim 10 wherein the molecular sieve is predominantly in the hydrogen form.

12. The process of claim 10 wherein the catalyst further comprises at least one Group VIII metal.

13. The process of claim 1 wherein the process is a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15–3000 psi (0.103–20.7 MPa) under dewaxing conditions with the catalyst.

14. The process of claim 13 wherein the molecular sieve is predominantly in the hydrogen form.

15. The process of claim 13 wherein the catalyst further comprises at least one Group VIII metal.

16. The process of claim 13 wherein said catalyst comprises a layered catalyst comprising a first layer comprising the molecular sieve and at least one Group VIII metal, and a second layer comprising an aluminosilicate molecular sieve which is more shape selective than the molecular sieve of said first layer.

17. The process of claim 1 wherein the process is a process for preparing a lubricating oil which comprises:
hydrocracking in a hydrocracking zone a hydrocarbonaceous feedstock to obtain an effluent comprising a hydrocracked oil; and
catalytically dewaxing said effluent comprising hydrocracked oil at a temperature of at least about 400° F. (204° C.) and at a pressure of from about 15 psig to about 3000 psig (0.103 to 20.7 MPa gauge) in the presence of added hydrogen gas with the catalyst.

18. The process of claim 17 wherein the molecular sieve is predominantly in the hydrogen form.

19. The process of claim 17 wherein the catalyst further comprises at least one Group VIII metal.

20. The process of claim 1 wherein the process is a process for isomerization dewaxing a raffinate comprising contacting said raffinate in the presence of added hydrogen under isomerization dewaxing conditions with the catalyst.

21. The process of claim 20 wherein the molecular sieve is predominantly in the hydrogen form.

22. The process of claim 20 wherein the catalyst further comprises at least one Group VIII metal.

23. The process of claim 20 wherein the raffinate is bright stock.

24. The process of claim 1 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C. under aromatic conversion conditions with the catalyst.

25. The process of claim 24 wherein the molecular sieve is substantially free of acid.

26. The process of claim 24 wherein the molecular sieve contains a Group VIII metal component.

27. The process of claim 1 wherein the process is a catalytic cracking process comprising contacting a hydrocarbon feedstock in a reaction zone under catalytic cracking conditions in the absence of added hydrogen with the catalyst.

28. The process of claim 27 wherein the molecular sieve is predominantly in the hydrogen form.

29. The process of claim 27 wherein the catalyst additionally comprises a large pore crystalline cracking component.

30. The process of claim 1 wherein the process is an isomerization process for isomerizing $C_4$ to $C_7$ hydrocarbons, comprising contacting a feed having normal and slightly branched $C_4$ to $C_7$ hydrocarbons under isomerizing conditions with the catalyst.

31. The process of claim 30 wherein the molecular sieve is predominantly in the hydrogen form.

32. The process of claim 30 wherein the molecular sieve has been impregnated with at least one Group VIII metal.

33. The process of claim 30 wherein the catalyst has been calcined in a steam/air mixture at an elevated temperature after impregnation of the Group VIII metal.

34. The process of claim 32 wherein the Group VIII metal is platinum.

35. The process of claim 1 wherein the process is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the catalyst.

36. The process of claim 35 wherein the molecular sieve is predominantly in the hydrogen form.

37. The process of claim 35 wherein the olefin is a $C_2$ to $C_4$ olefin.

38. The process of claim 37 wherein the aromatic hydrocarbon and olefin are present in a molar ratio of about 4:1 to about 20:1, respectively.

39. The process of claim 37 wherein the aromatic hydrocarbon is selected from the group consisting of benzene, toluene, ethylbenzene, xylene, naphthalene, naphthalene derivatives, dimethylnaphthalene or mixtures thereof.

40. The process of claim 1 wherein the process is a process for alkylating an aromatic hydrocarbon which comprises contacting under alkylation conditions an aromatic hydrocarbon with a $C_{20+}$ olefin under at least partial liquid phase conditions and in the presence of the catalyst.

41. The process of claim 40 wherein the molecular sieve is predominantly in the hydrogen form.

42. The process of claim 41 wherein the aromatic hydrocarbon and olefin are present in a molar ratio of about 1:15 to about 25:1, respectively.

43. The process of claim 41 wherein the aromatic hydrocarbon is selected from the group consisting of benzene, toluene, ethylbenzene, xylene, naphthalene, naphthalene derivatives, dimethylnaphthalene or mixtures thereof.

44. The process of claim 1 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

45. The process of claim 44 wherein the molecular sieve is predominantly in the hydrogen form.

46. The process of claim 44 wherein the aromatic hydrocarbon and the polyalkyl aromatic hydrocarbon are present in a molar ratio of from about 1:1 to about 25:1, respectively.

47. The process of claim 44 wherein the aromatic hydrocarbon is selected from the group consisting of benzene, toluene, ethylbenzene, xylene, or mixtures thereof.

48. The process of claim 44 wherein the polyalkyl aromatic hydrocarbon is a dialkylbenzene.

49. The process of claim 1 wherein the process is a process to convert paraffins to aromatics which comprises contacting paraffins under conditions which cause paraffins to convert to aromatics with a catalyst comprising the molecular sieve and gallium, zinc, or a compound of gallium or zinc.

50. The process of claim 1 wherein the process is a process for isomerizing olefins comprising contacting said olefin under conditions which cause isomerization of the olefin with the catalyst.

51. The process of claim 1 wherein the process is a process for isomerizing an isomerization feed comprising an aromatic $C_8$ stream of xylene isomers or mixtures of xylene isomers and ethylbenzene, wherein a more nearly equilibrium ratio of ortho-, meta and para-xylenes is obtained, said process comprising contacting said feed under isomerization conditions with the catalyst.

52. The process of claim 1 wherein the process is a process for oligomerizing olefins comprising contacting an olefin feed under oligomerization conditions with the catalyst.

53. A process for converting oxygenated hydrocarbons comprising contacting said oxygenated hydrocarbon under conditions to produce liquid products with a catalyst comprising A molecular sieve whose chemical composition, expressed in terms of mole ratios of oxides after calcination, is:

$Al_2O_3$: 1.0±0.2 $P_2O_5$: $x$ $SiO_2$: $y$ MeO; $z$ F where x has a value of 0 to 0.2, y has a value of 0 to 0.2, z has a value of 0.02 to 0.10 and Me represents at least one element, other than aluminum, phosphorus or silicon, which is capable of forming an oxide in coordination with ($AlO_2$) and ($PO_2$) oxide structural units in the molecular sieve, the molecular sieve having, after calcination and in a hydrated state, the X-ray diffraction lines of Table II.

54. The process of claim 53 wherein the oxygenated hydrocarbon is a lower alcohol.

55. The process of claim 54 wherein the lower alcohol is methanol.

56. The process of claim 1 wherein the process is a process for the production of higher molecular weight hydrocarbons from lower molecular weight hydrocarbons comprising the steps of:
 (a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and
 (b) withdrawing from said reaction zone a higher molecular weight hydrocarbon-containing stream.

57. The process of claim 56 wherein the metal or metal compound comprises a lanthanide or actinide metal or metal compound.

58. The process of claim 56 wherein the lower molecular weight hydrocarbon is methane.

* * * * *